«12» United States Patent
Fang

«10» Patent No.: US 10,519,078 B2
«45» Date of Patent: Dec. 31, 2019

«54» METHODS OF PRODUCING ETHYLENE AND PROPYLENE

«71» Applicant: Lyondell Chemical Technology, L.P., Houston, TX (US)

«72» Inventor: Linn Fang, Houston, TX (US)

«73» Assignee: Lyondell Chemical Technology, L.P., Houston, TX (US)

«*» Notice: Subject to any disclaimer, the term of this patent is extended or adjusted under 35 U.S.C. 154(b) by 0 days.

«21» Appl. No.: 16/165,630

«22» Filed: Oct. 19, 2018

«65» Prior Publication Data

US 2019/0119183 A1   Apr. 25, 2019

Related U.S. Application Data

«60» Provisional application No. 62/575,043, filed on Oct. 20, 2017.

«51» Int. Cl.
| C07C 4/06 | (2006.01) |
| C07C 4/02 | (2006.01) |
| B01J 29/85 | (2006.01) |
| C07C 7/04 | (2006.01) |

«52» U.S. Cl.
CPC ............... *C07C 4/06* (2013.01); *B01J 29/85* (2013.01); *C07C 7/04* (2013.01); *C07C 2529/40* (2013.01); *C07C 2529/82* (2013.01)

«58» Field of Classification Search
CPC .... C07C 4/06; C07C 7/04; C07C 7/02; C07C 4/02
See application file for complete search history.

«56» References Cited

U.S. PATENT DOCUMENTS

| 5,107,042 A | 4/1992 | Gaffney et al. | |
| 5,171,921 A | 12/1992 | Gaffney et al. | |
| 6,222,087 B1* | 4/2001 | Johnson | C10G 11/05 208/114 |
| 6,307,117 B1* | 10/2001 | Tsunoda | B01J 29/061 585/651 |
| 2010/0256431 A1* | 10/2010 | Nesterenko | B01J 29/06 585/330 |
| 2012/0041243 A1* | 2/2012 | Senetar | C07C 1/20 585/251 |

* cited by examiner

*Primary Examiner* — Youngsul Jeong

«57» ABSTRACT

Methods of producing propylene and/or ethylene. The methods can include contacting a mixture of C4+ compounds with a catalyst, such as a fixed bed catalyst, that includes a phosphorus treated zeolite. The mixture of C4+ compounds can include a plurality of C4 olefins, a plurality of C5 olefins, and/or a plurality of C6+ olefins.

20 Claims, 1 Drawing Sheet ered to as fuels of various 20 C4+ compounds to at least one of ethylene and propylene.
METHODS OF PRODUCING ETHYLENE AND PROPYLENE

CROSS-REFERENCE TO RELATED APPLICATIONS

This application claims the benefit of priority to U.S. Provisional Patent Application No. 62/575,043 filed on Oct. 20, 2017, which is incorporated herein by reference in its entirety.

BACKGROUND OF THE INVENTION

Current methanol-to-olefin processes typically are designed in a manner that produces ethylene and/or propylene. The by-products from the methanol-to-olefin processes, however, usually include C4, C5, and C6+ streams that can be rich in olefins. A typical composition may include a weight ratio of C4/C5/C6 olefins of about 5:2:1. These C4+ streams often include at least 80 weight % of olefins. These by-products are typically disposed of as fuels of various types, or converted to fuel components, such as octane enhancers, normally after being separated into two or more fractions. It would be advantageous, however, to convert these streams into commercially valuable olefins, such as propylene and/or ethylene.

Even though it is theoretically possible, these streams typically are not suitable for use as an olefin cracker feedstock, due at least in part to the high content of olefins. It is also possible that these streams may be used for producing light olefins via metathesis processes, but some isomers in each group of the C4, C5, and C6 olefins are undesirable. Furthermore, the oxygenates and dienes/acetylenes contained in the streams, which are inherent of MTO processes, should be removed prior to the foregoing processes, which results in increased cost, increased waste generation, or a combination thereof.

Methods are known for producing commercially important olefins, such as ethylene and propylene. Such methods include steam cracking, propane dehydrogenation, and various refinery catalytic cracking operations. Each of these procedures has one or more disadvantages. For example, propylene yields from steam cracking typically are not very high, and usually are not substantially improved by recycling. Also, purification of non-propylene products may be required, which can be costly, and such products usually have only fuel value. Propane dehydrogenation processes usually are characterized by rapid catalyst coking, which can require frequent, costly regenerations. Also, reasonable conversions typically require sub-atmospheric pressures, and propane can be difficult to separate from propylene. Moreover, propylene supplies from catalytic conversions are uncertain, and transportation and/or purification can present problems.

Therefore, methods are desired that convert the by-products, including pre-fractionated by-products, of chemical processes, such as methanol-to-olefin processes, to ethylene and/or propylene in an efficient, cost-effective, and/or facile manner.

SUMMARY OF THE INVENTION

Figure 1:
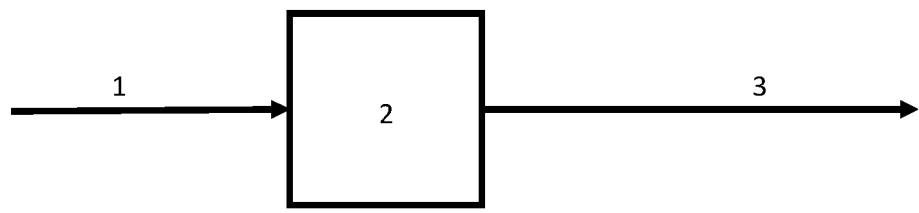
FIG. 1 depicts an embodiment of a process configuration.

Provided herein are methods of producing at least one of ethylene and propylene. In embodiments, the methods comprise providing a first mixture of C4+ compounds comprising a plurality of C4+ olefins in an amount of at least 30% by weight of the mixture; and contacting the first mixture of C4+ compounds with a catalyst comprising a phosphorus treated zeolite to convert at least a portion of the mixture of C4+ compounds to at least one of ethylene and propylene. The first mixture of C4+ compounds may include C4 olefins, C5 olefins, and C6 olefins. In one embodiment, the methods further comprise separating the ethylene and/or the propylene from the first mixture of C4+ compounds to form a second mixture of C4+ compounds, and contacting the second mixture of C4+ compounds with the catalyst to convert at least a portion of the second mixture of C4+ compounds to at least one of ethylene and propylene. The methods also may further comprise separating the ethylene and/or the propylene from the second mixture of C4+ compounds to form a third mixture of C4+ compounds, and contacting the third mixture of C4+ compounds with the catalyst to convert at least a portion of the third mixture of C4+ compounds to at least one of ethylene and propylene. The catalyst may be a fixed bed catalyst or a solid catalyst.

In embodiments, the methods comprise contacting a tailstream of a methanol-to-olefin process with a catalyst comprising a phosphorus treated zeolite, wherein the tailstream comprises a plurality of C4+ compounds, and the catalyst converts at least a portion of the plurality of C4+ compounds to at least one of ethylene and propylene. In one embodiment, the methods further comprise separating the ethylene and/or propylene from the tailstream to form a first mixture of C4+ compounds, and contacting the first mixture of C4+ compounds with the catalyst to convert at least a portion of the first mixture of C4+ compounds to at least one of ethylene and propylene. The methods also may further comprise separating the ethylene and/or propylene from the first mixture of C4+ compounds to form a second mixture of C4+ compounds, and contacting the second mixture of C4+ compounds with the catalyst to convert at least a portion of the second mixture of C4+ compounds to at least one of ethylene and propylene. The catalyst may be a fixed bed catalyst or a solid catalyst.

In embodiments, the methods comprise providing a first mixture of C4+ compounds comprising a first plurality of C4+ olefins in an amount of at least 30% by weight of the first mixture of C4+ compounds; and contacting the first mixture of C4+ compounds with a catalyst comprising a phosphorus treated zeolite to convert the first mixture to a reactor effluent comprising a second plurality of C4+ olefins and at least one of ethylene and propylene, wherein at least 25% by weight of the first plurality of C4+ olefins of the first mixture is converted to at least one of ethylene and propylene; and contacting the reactor effluent with the catalyst to convert at least a portion of the second plurality of C4+ olefins to at least one of ethylene and propylene. The catalyst may be a fixed bed catalyst or a solid catalyst.

DETAILED DESCRIPTION OF THE INVENTION

Provided herein are methods for producing at least one of ethylene and propylene from a mixture of C4+ compounds that overcome one or more of the disadvantages associated with other methods for producing commercially important olefins. In embodiments, the methods provided herein produce a mixture of ethylene and propylene. The mixture of ethylene and propylene may have a weight ratio of propylene:ethylene of about 1:1 to about 6:1, or about 1.4:1 to about 4.8:1.

The mixture of C4+ compounds, which may be a tail-stream of a chemical process (such as a methanol-to-olefin process) may be contacted with a catalyst comprising a phosphorus treated zeolite to convert at least a portion of the mixture of C4+ compounds to at least one of ethylene and propylene. The ethylene and/or propylene then may be separated from the mixture of C4+ compounds, and the mixture of C4+ compounds may be contacted with the catalyst a second time. In addition to the ethylene and/or propylene, other, non-C4+ compounds, including, but not limited to, coke, $C_2H_6$, and $C_3H_8$, may be removed from the mixture of C4+ compounds after one or more of the contacting steps. The contacting step may be repeated any number of times. In one embodiment, the contacting step is repeated until a desired conversion rate of the mixture of C4+ compounds, or a portion thereof, to at least one of propylene and ethylene is achieved.

In embodiments, the reactor effluent is recycled to convert more C4+ compounds to propylene and ethylene, and a purge may be removed from the recycle stream to prevent paraffins and/or aromatics from building up, for example, at over 50% by weight.

Generally, the mixture of C4+ compounds may be contacted with a catalyst comprising phosphorus treated zeolite at any combination of temperature and pressure that is effective to convert at least a portion of the mixture of C4+ compounds to at least one of ethylene and propylene. In one embodiment, the contacting occurs at a temperature of about 600° F. to about 1,300° F., about 815° F. to about 1,300° F., about 900° F. to about 1,300° F., or about 1,050° F. to about 1,200° F. In another embodiment, the contacting occurs at a temperature of about 700° F. to about 1,175° F. In a further embodiment, the contacting occurs at a temperature of about 700° F. to about 950° F. In yet another embodiment, the contacting occurs at a temperature of about 700° F. to about 850° F. In a still further embodiment, the contacting occurs at a temperature of about 700° F. to about 750° F. In additional embodiments, the contacting occurs at a temperature of about 800° F. to about 1,175° F. In some embodiments, the contacting occurs at a temperature of about 900° F. to about 1,175° F. In further embodiments, the contacting occurs at a temperature of about 1,000° F. to about 1,175° F. In a particular embodiment, the contacting occurs at a temperature of about 1,175° F. In yet another particular embodiment, the contacting occurs at a temperature of about 1,100° F.

In one embodiment, the contacting occurs at ambient pressure. In another embodiment, the contacting occurs at a pressure of about 1 psig to about 30 psig. In yet another embodiment, the contacting occurs at a pressure of about 5 psig to about 30 psig. In a still further embodiment, the contacting occurs at a pressure of about 10 psig to about 20 psig. In an additional embodiment, the contacting occurs at a pressure of about 15 psig. In further embodiments, the contacting occurs at a pressure of about 12 psig.

In one embodiment, the contacting occurs at a temperature of about 600° F. to about 1,300° F., about 700° F. to about 1,175° F., about 700° F. to about 950° F., about 700° F. to about 850° F., about 700° F. to about 750° F., about 800° F. to about 1,175° F., about 900° F. to about 1,175° F., about 1,000° F. to about 1,175° F., or about 1,175° F., and at ambient pressure.

In one embodiment, the contacting occurs at a temperature of about 600° F. to about 1,300° F., about 700° F. to about 1,175° F., about 700° F. to about 950° F., about 700° F. to about 850° F., about 700° F. to about 750° F., about 800° F. to about 1,175° F., about 900° F. to about 1,175° F., about 1,000° F. to about 1,175° F., or about 1,175° F., and a pressure of about 1 psig to about 30 psig.

In one embodiment, the contacting occurs at a temperature of about 600° F. to about 1,300° F., about 700° F. to about 1,175° F., about 700° F. to about 950° F., about 700° F. to about 850° F., about 700° F. to about 750° F., about 800° F. to about 1,175° F., about 900° F. to about 1,175° F., about 1,000° F. to about 1,175° F., or about 1,175° F., and a pressure of about 5 psig to about 30 psig.

In one embodiment, the contacting occurs at a temperature of about 600° F. to about 1,300° F., about 700° F. to about 1,175° F., about 700° F. to about 950° F., about 700° F. to about 850° F., about 700° F. to about 750° F., about 800° F. to about 1,175° F., about 900° F. to about 1,175° F., about 1,000° F. to about 1,175° F., or about 1,175° F., and a pressure of about 10 psig to about 30 psig.

In one embodiment, the contacting occurs at a temperature of about 600° F. to about 1,300° F., about 700° F. to about 1,175° F., about 700° F. to about 950° F., about 700° F. to about 850° F., about 700° F. to about 750° F., about 800° F. to about 1,175° F., about 900° F. to about 1,175° F., about 1,000° F. to about 1,175° F., or about 1,175° F., and a pressure of about 15 psig.

In one embodiment, the contacting occurs at a temperature of about 1100° F., and a pressure of about 12 psig.

The hydrocarbon feed weight hourly space velocity (based on the zeolite component of the catalyst) may be about 1 to about 750 $h^{-1}$, about 1 to about 500 $h^{-1}$, about 1 to about 400 $hr^{-1}$, about 200 to about 400 $hr^{-1}$, about 300 to about 400 $hr^{-1}$, or about 316 $hr^{-1}$.

The hydrocarbon feed weight hourly space velocity (based on the zeolite component of the catalyst) may be about 1 to about 200 $hr^{-1}$, about 30 to about 130 $hr^{-1}$, about 40 to about 120 $hr^{-1}$, about 40 $hr^{-1}$, or about 116 $hr^{-1}$.

In one embodiment, the contacting occurs at a temperature of about 1100° F., a pressure of about 12 psig, and a feed weight hourly space velocity (based on the zeolite component of the catalyst) of about 40 $hr^{-1}$, or about 116 $hr^{-1}$.

Mixture of C4+ Compounds

In embodiments, the mixture of C4+ compounds comprises at least one of a plurality of olefins and a plurality of paraffins.

In one embodiment, the mixture of C4+ compounds comprises a plurality of C4 olefins. In another embodiment, the mixture of C4+ compounds comprises a plurality of C4 olefins and a plurality of C5 olefins. In yet another embodiment, the mixture of C4+ compounds comprises a plurality of C4 olefins, a plurality of C5 olefins, and a plurality of C6+ olefins.

In one embodiment, the mixture of C4+ compounds comprises a plurality of C4 olefins in an amount of about 30% to 100% by weight of the mixture of C4+ compounds, about 35% to 100% by weight of the mixture of C4+ compounds, about 40% to 100% by weight of the mixture of C4+ compounds, about 50% to 100% by weight of the mixture of C4+ compounds, about 60% to 100% by weight of the mixture of C4+ compounds, about 70% to 100% by weight of the mixture of C4+ compounds, or about 75% to 100% by weight of the mixture of C4+ compounds. Therefore, the mixture of C4+ compounds may comprise a plurality of C4 olefins in an amount of at least 30%, at least 35%, at least 40%, at least 50%, at least 60%, at least 70%, or at least 75% by weight of the mixture of C4+ compounds.

In one embodiment, the mixture of C4+ compounds comprises a plurality of C4+ olefins in an amount of about 30% to 100% by weight of the mixture of C4+ compounds, about 35% to 100% by weight of the mixture of C4+ compounds, about 40% to 100% by weight of the mixture of C4+ compounds, about 50% to 100% by weight of the mixture of C4+ compounds, about 60% to 100% by weight of the mixture of C4+ compounds, about 70% to 100% by weight of the mixture of C4+ compounds, or about 75% to 100% by weight of the mixture of C4+ compounds. Therefore, the mixture of C4+ compounds may comprise a plurality of C4+ olefins in an amount of at least 30%, at least 35%, at least 40%, at least 50%, at least 60%, at least 70%, or at least 75% by weight of the mixture of C4+ compounds.

In one embodiment, the mixture of C4+ compounds comprises a plurality of C5 olefins and a plurality of C6+ olefins in a combined amount of about 10% to about 50% by weight of the mixture of C4+ compounds, about 15% to about 50% by weight of the mixture of C4+ compounds, about 20% to about 50% by weight of the mixture of C4+ compounds, or about 25% to about 50% by weight of the mixture of C4+ compounds.

In one embodiment, the mixture of C4+ compounds comprises a plurality of C6+ olefins in an amount of about 3% to about 50% by weight of the mixture of C4+ compounds, about 5% to about 50% by weight of the mixture of C4+ compounds, about 15% to about 50% by weight of the mixture of C4+ compounds, about 20% to about 50% by weight of the mixture of C4+ compounds, or about 25% to about 50% by weight of the mixture of C4+ compounds. The plurality of C6+ olefins may be present at an amount of at least about 5%, at least about 10%, at least about 15%, at least about 20%, at least about 25%, at least about 30%, at least about 35%, at least about 40%, at least about 45%, or at least about 50%, by weight of the mixture of C4+ compounds.

In one embodiment, the mixture of C4+ compounds comprises C4 olefins in an amount of about 30% to 100% by weight of the mixture of C4+ compounds, about 40% to 100% by weight of the mixture of C4+ compounds, about 50% to 100% by weight of the mixture of C4+ compounds, about 60% to 100% by weight of the mixture of C4+ compounds, about 70% to 100% by weight of the mixture of C4+ compounds, or about 75% to 100% by weight of the mixture of C4+ compounds, and a plurality of C5 olefins and a plurality of C6+ olefins in a combined amount of about 10% to about 50% by weight of the mixture of C4+ compounds.

The mixture of C4+ compounds may be a tailstream, or part of a tailstream, of a chemical process, such as a methanol-to-olefin process.

The mixture of C4+ compounds may be part of a feed stream that includes a diluent. The diluent, in embodiments, is present in the feed stream in an amount of about 5% to about 40% by weight of the mixture of C4+ compounds, about 5% to about 35% by weight of the C4+ compounds, about 5% to about 10% by weight of the C4+ compounds, about 20% to about 35% by weight of the C4+ compounds, about 25% to about 35% by weight of the C4+ compounds, or about 30% by weight of the mixture of C4+ compounds. In one embodiment, the diluent comprises steam.

Conversion Rates

Unless otherwise noted, the phrase "is converted" refers to conversion rates obtained after a contacting step, as described herein, is performed once, and the contact step may be the first contacting step, second contacting step, etc. Higher cumulative conversion rates may be achieved by repeating the contacting step one or more times, as described herein. The cumulative conversion rates provided herein are indicated by the phrase "is cumulatively converted," and are based on the total weight percentage of an original amount of a particular material, such as a plurality of C4+ olefins, that is converted to ethylene and/or propylene after the contacting step is repeated, typically 1 to 10 times.

The phrase "is converted to at least one of ethylene and propylene" indicates that the compounds have undergone a conversion reaction with a C2/C3 olefin selectivity that results in the indicated percentages. For example, if 59.5% of a plurality of C4, C5, and C6 olefins is converted with a C2/C3 olefin selectivity of 50%, then 29.75%, by weight, of the plurality of C4, C5, and C6 olefins is converted to at least one of ethylene and propylene.

In embodiments, the mixture of C4+ compounds comprises a plurality of C4+ olefins, and at least 15% by weight, at least 20% by weight, at least 25% by weight, at least 35% by weight, at least 45% by weight, at least 55% by weight, at least 65% by weight, or at least 75% by weight of the plurality of C4+ olefins is converted to at least one of ethylene and propylene.

In embodiments, the mixture of C4+ compounds comprises a plurality of C4, C5, and C6 olefins, and at least 15%, at least 20%, at least 25%, at least 35% by weight, at least 40% by weight, at least 50% by weight, or at least 60% by weight of the plurality of C4, C5, and C6 olefins (based on the total weight of the plurality of C4, C5, and C6 olefins) is converted to at least one of ethylene and propylene.

Catalysts

Generally, the catalysts provided herein include phosphorus treated zeolite catalysts. In embodiments, the phosphorus treated zeolite comprises phosphorus in an amount of about 0.1 to about 10%, by weight of the phosphorus treated zeolite, about 0.1% to about 8%, by weight of the phosphorus treated zeolite, about 0.1% to about 6%, by weight of the phosphorus treated zeolite, about 0.1% to about 5% by weight of the phosphorus treated zeolite, about 1% to about 4%, by weight of the phosphorus treated zeolite, about 1% to about 3%, by weight of the phosphorus treated zeolite, or about 1.2%, by weight of the phosphorus treated zeolite.

The phosphorus treated zeolite may be made by contacting a zeolite with a phosphorus containing compound. The phosphorus containing compound may be an acid. Examples of phosphorus containing compounds include, but are not limited to, $H_3PO_4$, ammonium hydrogen phosphates, such as $(NH_4)_2HPO_4$ or $(NH_4)H_2PO_4$, phosphonic acid (also called phosphorous acid) ($H_3PO_3$), or a combination thereof. The zeolite may be contacted with the phosphorus containing compound in an amount sufficient to impart the catalyst with a desired phosphorus content. The zeolite may be contacted with water before, during, or after the zeolite is contacted with the phosphorus containing compound. The amount of water may be an amount sufficient to wet the zeolite only. After being contacted with a phosphorus containing compound and/or water, the zeolite may be dried by any means known in the art.

The phosphorus treated zeolite may be combined with a binder. The binder may include silica, kaolin, calcium, bentonite, alumina, silica aluminate, or a combination thereof. In one embodiment, the binder includes bentonite, silica, and kaolin. The bentonite, silica, and kaolin may be present in the binder at a bentonite:silica:kaolin weight ratio of about 1:(8-16):(20-28); about 1:(10-14):(22-26); or about 1:12:24.

The phosphorus treated zeolite, in embodiments, is present in the catalyst in an amount of about 1% to about 50% by weight, based on the combined weight of the phosphorus treated zeolite and the binder. In further embodiments, the phosphorus treated zeolite is present in the catalyst in an amount of about 5% to about 40% by weight, based on the combined weight of the phosphorus treated zeolite and the binder. In additional embodiments, the phosphorus treated zeolite is present in the catalyst in an amount of about 5% to about 30% by weight, based on the combined weight of the phosphorus treated zeolite and the binder. In a particular embodiment, the phosphorus treated zeolite is present in the catalyst in an amount of about 10% to about 25% by weight, based on the combined weight of the phosphorus treated zeolite and the binder. In some embodiments, the phosphorus treated zeolite is present in the catalyst in an amount of about 15% to about 30% by weight, based on the combined weight of the phosphorus treated zeolite and the binder. In particular embodiments, the phosphorus treated zeolite is present in the catalyst in an amount of about 20% to about 30% by weight, based on the combined weight of the phosphorus treated zeolite and the binder. In one embodiment, the phosphorus treated zeolite is present in the catalyst in an amount of about 25% by weight, based on the combined weight of the phosphorus treated zeolite and the binder.

The phosphorus treated zeolite and binder may be contacted with an amount of water sufficient to form a paste, and the paste may be mixed by any means known in the art in order to form a paste that is at least substantially homogeneous.

The at least substantially homogeneous paste may be extruded into extrudates of any desired size. The extrudates also may be calcined, steamed, or a combination thereof. The calcining may be performed at a temperature of about 500° C. to about 700° C., or about 600° C. The steam treatment, in one embodiment, is conducted prior to contacting the catalyst with a mixture of C4+ hydrocarbons. The steam treatment may be performed at a temperature of about 800° F. to about 1200° F., 500° C. to 700° C., or about 550° C. to about 600° C., and at a pressure of about 1 to about 5 atmospheres, or about 1.5 to about 3 atmospheres, for about 1 to about 48 hours, or about 15 to about 30 hours.

The extrudates generally may have any desired size. For lab testing, the extrudates may have a size of 6 to 20 mesh. In one embodiment, the catalyst is a fixed bed catalyst, and the extrudates are particles having an average diameter of about 1 mm to about 5 mm. The particles may be at least substantially spherical, but the use of the term "diameter" is not intended to convey that the particles necessarily are or include at least substantially spherical particles. When the particles are not at least substantially spherical, the term "diameter" refers to the average largest dimension of the particles.

The term "zeolite", as used herein, generally refers to porous materials, such as hydrated, crystalline metal aluminosilicates, and/or molecular sieves of a non-zeolitic material. Thus, zeolites include a group of natural or synthetic hydrated aluminosilicate minerals that contain alkali and alkaline metals. Zeolites may be characterized by a framework structure that encloses interconnected cavities occupied by ion-exchangeable large metal cations, such as potassium and water molecules permitting reversible dehydration.

In embodiments, the zeolite comprises a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms may be equal to about 2. The framework may exhibit a negative electrovalence that can be balanced by the inclusion of cations within the crystal. The cations may include potassium cations, ammonium cations, or a combination thereof.

The formula of the zeolite may vary without changing the crystalline structure. In an embodiment, the mole ratio of silicon dioxide to aluminum oxide ($SiO_2/Al_2O_3$) in the zeolite may vary from about 10 to about 200. In one embodiment, the molar $SiO_2:Al_2O_3$ ratio is about 20 to about 60.

In one embodiment, the zeolite has an alkali metal content of less than about 0.5% by weight of the zeolite. Alkali metals are those in Group IA or Group IIA of the periodic table, such as lithium, sodium, potassium, calcium, etc.

In embodiments, the zeolite is selected from ZSM-5, ZSM-11, ZSM-22, ZSM-23, ZSM-35, ZSM-48, ZSM-57, SUZ-4, SSZ-23; SSZ-25; SSZ-28, SSZ-32, SSZ-36, ZSM-3, ZSM-4, ZSM-10, ZSM-12, ZSM-20, zeolite beta, zeolite omega, zeolite L, zeolite X, zeolite Y, REY, USY, RE-USY, mordenite, LZ-210, LZ-210-M, LZ-210-T, LZ-210-A, SSZ-24, SSZ-26, SSZ-31, SSZ-33, SSZ-35, SSZ-37, SSZ-41, SSZ-42, SSZ-44, MCM-58, or a combination thereof. In one embodiment, the zeolite is ZSM-5. The ZSM-5 may be the protonic form of ZSM-5.

In embodiments, the catalyst comprises a phosphorus treated ZSM-5 zeolite. In one embodiment, the catalyst comprises a phosphorus treated ZSM-5 zeolite having a Si/Al ratio of about 20 to about 60. In another embodiment, the catalyst comprises a phosphorus treated ZSM-5 zeolite having an alkali metal content of less than about 0.5% by weight of the ZSM-5 zeolite.

In embodiments, the catalyst is a fixed bed catalyst. In one embodiment, the catalyst is a solid catalyst. The catalyst may be arranged as a fluidized bed reactor.

In embodiments, the catalyst comprises about 15% to about 40%, by weight, or about 20% to about 30%, by weight, of the protonic form of ZSM-5; about 0.001% to about 0.5%, by weight, of alkali metals; and about 1% to about 4%, by weight, of phosphorus. The remaining portion of the catalyst may comprise a binder, matrix, and/or filler, which may be selected from non-zeolite materials suitable for applications in a fixed bed or fluidized bed. Non-limiting examples of non-zeolite materials include silica sol, kaolin, amorphous alumina, or a combination thereof.

In embodiments, the Si/Al ratio of the catalyst may be about 15 to about 100, or about 25 to about 50.

In embodiments, the catalyst comprises a steam treated catalyst comprising [1] about 15% to about 40%, by weight, or about 20% to about 30%, by weight, of the protonic form of ZSM-5; [2] about 0.001% to about 0.5, by weight, of alkali metals; [3] about 1% to about 4%, by weight, of phosphorus; and [4] a binder, matrix, and/or filler selected from silica sol, kaolin, amorphous alumina, or a combination thereof; wherein the Si/Al ratio of the catalyst is about 15 to about 100, or about 25 to about 50.

In embodiments, a catalyst system used in the processes described herein includes [1] a class of zeolite commonly known as protonic ZSM-5 or H-ZSM-5 at about 10 to about 40%, by weight (or about 20% to about 30%, by weight), as solid particles (including, but not limited to, solid particles that are spherical, cylindrical, lobed extrudates, etc.), and [2] a binder material, such as silica, kaolin, silica aluminate, alumina, bentonite, or a combination thereof. In some embodiments, the catalyst system is dosed with phosphorus, such as about 1% to about 3%, by weight, of the catalyst, resulting in a catalyst system symbolized as PH-ZSM-5. In some embodiments, the catalyst is treated with steaming before use.

In some embodiments, the catalyst is installed in a stationary enclosure wherein a feedstock is brought into contact with the stationary enclosure. In some embodiments, the catalyst is disposed in a fixed bed reactor. In some embodiments, the catalyst is forced into and/or through an enclosed space as a co-current flow or counter-current flow to the hydrocarbon feedstock, wherein a feedstock is brought into contact with the catalyst. In some embodiments, the catalyst is disposed in a fluidized bed reactor.

In embodiments, as depicted at FIG. 1, a feedstock 1 is brought into contact with a catalyst in a reaction zone 2 in a "once through mode," wherein the processed stream 3 exits the reaction zone 2 after contacting the catalyst in the reaction zone 2.

Figure 2:
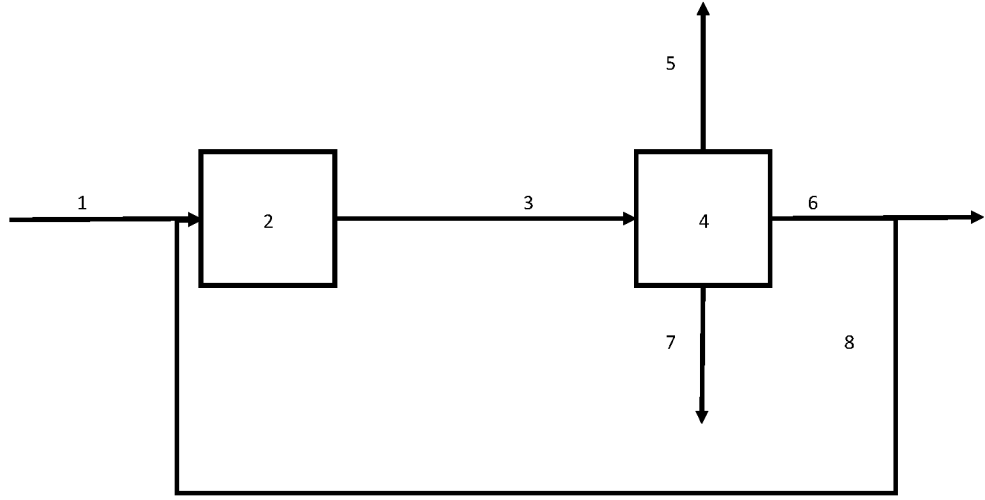
FIG. 2 depicts an embodiment of a process configuration.

In embodiments, as depicted at FIG. 2, a feedstock 1 is brought into contact with a catalyst in a reaction zone 2, and the processed stream 3 is forwarded to a fractionator 4, which separates the processed stream 3 into a light fraction stream 5, a middle fraction stream 6, and a heavy fraction stream 7. The middle fraction stream 6 is returned to the reaction zone 2 as additional feed up to 100% of the flow.

In embodiments, the catalysts provided herein facilitate, at least in part, a predictable and/or quantitative redistribution of the olefins from C2 to C6+ specific to reaction conditions, including contact time, temperature, and pressure. Therefore, in some embodiments, at least a portion of the mixture of C4+ olefins that lacks C2/C3 olefins, may, upon contacting a catalyst described herein, be converted to C2/C3 olefins. The mixture of C4+ olefins may include a plurality of C4, C5, and C6 olefins. The reaction conditions may be varied to achieve a desired ratio of C2/C3 olefins.

Prediction methodologies have been established, which match actual reaction data (see Examples). The parameters for two different conditions are depicted at Table 1, and Table 2 depicts the predicted results with a feed composition resembling a fresh MTO mixed C4+ byproduct stream combined with an expected recycled C4+ stream after the removal of C2/C3 hydrocarbons. The impurities typically contained in MTO byproducts, including, but not limited to, oxygenates, moisture and dienes/acetylenes at the typical concentrations, will not substantially impede embodiments of the processes described herein, which may result in a cost savings at least commensurate with the expenses associated with feed pretreating and/or conditioning regarding these impurities.

TABLE 1

Reaction Conditions

| Conditions | Case 1 | Case 2 |
|---|---|---|
| Temperature, F. | 1100 | 1100 |
| Pressure, psig | 12 | 12 |
| WHSV | 116 | 40 |

TABLE 2

Reaction Yields

| | Feed in weight | Effluent in weight Case 1 | Effluent in weight Case 2 |
|---|---|---|---|
| Coke | 0.00 | 0.01 | 0.02 |
| H2 | 0.00 | 0.03 | 0.60 |
| C2= | 0.00 | 4.90 | 7.95 |
| C3= | 0.03 | 17.80 | 21.86 |
| C4=s | 29.40 | 22.12 | 14.78 |
| C5=s | 20.13 | 8.04 | 5.62 |
| C6=s | 0.89 | 0.00 | 0.00 |
| C1-C5 Paraffins | 45.29 | 40.44 | 39.12 |

TABLE 2-continued

Reaction Yields

| | Feed in weight | Effluent in weight Case 1 | Effluent in weight Case 2 |
|---|---|---|---|
| Heavies | 4.26 | 6.66 | 10.05 |
| Sum | 100.00 | 100.00 | 100.00 |
| C4/C5/C6 Olefin Conversion | | 40.2% | 59.5% |

While the present invention may be embodied in many different forms, disclosed herein are specific illustrative embodiments thereof that exemplify the principles of the invention. It should be emphasized that the present invention is not limited to the specific embodiments illustrated.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Preparation of Catalyst

To 200 g of CBV5524G zeolite powder (Zeolyst, USA), $H_3PO_4$ and water were added. The $H_3PO_4$ was added in an amount sufficient to provide an equivalent of 1.2% by weight phosphorus, based on the weight of the dry zeolite powder. Water was added in an amount sufficient to wet the powder barely (incipient wetness). The zeolite powder was then dried overnight at 120° C.

To the zeolite powder was added 16 g of bentonite clay, 202 g of Davison 633 silica gel (VWR, USA), 388 g of kaolin, and an amount of DI water sufficient to make a viscous paste. These components were then mixed with a mixer (Caleva) to form a homogeneous paste.

The paste was then extruded into 2 mm OD extrudates with a high torque extruder (Bonnot BA373). The extrudates were then calcined at 600° C. in air, and then steamed for 24 hours at 575° C.

Example 2—Conversion of Olefins

In this example, a feedstock was brought into contact with a catalyst in a reaction zone to produce a processed stream. This example, therefore, was an embodiment of the process depicted at FIG. 1. Specifically, the catalyst of Example 1 was configured in a fixed bed reactor (i.e., reaction zone 2 of FIG. 1) containing 10 grams of catalyst through which a mixture of C5 olefins (i.e., feedstock 1 of FIG. 1) was fed at 1 psig, and 997° F. The olefin feed WHSV was 9.73 on a dry basis. Steam was fed at a WHSV of 0.6 to maintain catalyst activity. The overall conversion of C5 olefins was 89.8% (i.e., processed stream 3 of FIG. 1). There was no recycle of products back to the feed. The reaction selectivities are listed below, and were calculated from the composition of the processed stream (i.e., processed stream 3 of FIG. 1):

| Component | Selectivity, wt %, dry basis |
|---|---|
| coke | 0.05 |
| hydrogen | 0.04 |
| methane | 0.13 |
| ethylene | 11.18 |
| ethane | 0.14 |
| propylene | 31.18 |
| propane | 4.06 |
| isobutane | 2.78 |
| butadiene | 0.21 |
| n-butane | 1.85 |
| C4 olefins | 24.23 |
| C5 paraffins | 4.64 |
| C6 | 7.09 |
| benzene | 1.74 |
| C7 | 2.88 |
| toluene | 2.87 |
| C8 non aromatics | 1.09 |
| C8 aromatics | 2.89 |
| C9+ | 0.95 |
| Sum | 100.00 |

Example 3—Recycle of Heavy Olefins

The reaction of this example was an embodiment of the process depicted at FIG. 2. The catalyst of example 1 was configured in a fixed bed reactor (i.e., reaction zone 2 of FIG. 2) containing 10 grams of catalyst through which a mixture of C4 olefins and paraffins (i.e., feedstock 1 of FIG. 2) was fed at 6 psig and 1000° F. The C4 feed was at the WHSV of 18 (on fresh feed basis). The reactor effluent was fed to a series of distillation towers (i.e., fractionator 4 of FIG. 2) so the ethylene and propylene could be recovered as a distillate (i.e., middle fraction stream 6 of FIG. 2).

The distillation towers produced three additional streams: a purge stream (i.e., light fraction stream 5 of FIG. 2), another purge (i.e., heavy fraction stream 7 of FIG. 2), and a recycle stream (i.e., stream 8 of FIG. 2). As in FIG. 2, the recycle stream was sent back to the fixed bed reactor (i.e., reaction zone 2) after being combined with the feedstock 1.

The table below shows the component mass flows.

| Components | Fresh feed Grams/Hour | Recycle Grams/Hour | Product Grams/Hour | Purges Grams/Hour |
|---|---|---|---|---|
| Coke | | | 0.121 | 0 |
| H2 | | | 0.027 | 0 |
| Methane | | | 0.126 | 0 |
| Ethylene | | | 6.720 | 0 |
| Ethane | | | 0.078 | 0 |
| Propylene | | 0.144 | 65.200 | 0.034 |
| Propane | | 0 | 1.948 | 0 |
| Isobutane | | 1.009 | 1.959 | 0.241 |
| Butadiene | | 0.451 | 0.238 | 0.108 |
| n-butane | 29.093 | 76.011 | 14.092 | 18.137 |
| Butenes | 151.178 | 81.226 | 26.02 | 19.382 |
| Pentenes | | 38.988 | 1.368 | 9.303 |
| Pentanes | | 6.949 | 0.184 | 1.658 |
| C6 non aromatic | | 14.123 | 0.080 | 3.370 |
| Benzene | | 1.199 | 0.031 | 0.286 |
| C7 non-aromatic | | 9.181 | 0.008 | 2.191 |
| Toluene | | .95 | 0.015 | 0.227 |
| C8 | | 12.636 | 0.018 | 3.015 |
| C9 | | 10.733 | 0.003 | 2.561 |
| C10+ | | 6.391 | 0 | 1.525 |
| Sum | 180.27 | 259.99 | 118.24 | 62.04 |

The propylene yield based on olefin fresh feed was 43 wt %. The ethylene yield was 4 wt %.

What is claimed is:

1. A method of producing at least one of ethylene and propylene, the method comprising:
   providing a first mixture of C4+ compounds comprising a plurality of C4+ olefins in an amount of at least 30% by weight of the first mixture of C4+ compounds; and
   contacting the first mixture of C4+ compounds with a catalyst comprising:
   (a) a phosphorus treated zeolite, wherein the phosphorus treated zeolite comprises an alkali metal, and wherein the alkali metal is present in an amount no greater than about 0.5% by weight of the phosphorus treated zeolite, and
   (b) a binder, wherein the binder comprises bentonite, silica and kaolin, and wherein the bentonite, silica and kaolin are present in the binder at a bentonite:silica:kaolin weight ratio of about 1:8-16:20-28,
   to convert at least a portion of the first mixture of C4+ compounds to at least one of ethylene and propylene, thereby producing a first effluent comprising at least one of ethylene and propylene;
   wherein at least 15% by weight of the plurality of C4+ olefins is converted to at least one of ethylene and propylene.

2. The method of claim 1, wherein the first mixture of C4+ compounds comprises a plurality of C4+ olefins in an amount of at least 35% by weight of the first mixture of C4+ compounds.

3. The method of claim 1 wherein the first mixture of C4+ compounds comprises a plurality of C5 olefins in an amount of at least 10% by weight of the first mixture of C4+ compounds.

4. The method of claim 1 wherein the first mixture of C4+ compounds comprises a plurality of C6+ olefins in an amount of at least 5% by weight of the first mixture of C4+ compounds.

5. The method of claim 1, further comprising separating the ethylene and/or the propylene from the first effluent to form a second mixture of C4+ compounds, and contacting the second mixture of C4+ compounds with the catalyst to convert at least a portion of the second mixture of C4+ compounds to at least one of ethylene and propylene, thereby producing a second effluent comprising at least one of ethylene and propylene.

6. The method of claim 5, further comprising separating the ethylene and/or the propylene from the second effluent to form a third mixture of C4+ compounds, and contacting the third mixture of C4+ compounds with the catalyst to convert at least a portion of the third mixture of C4+ compounds to at least one of ethylene and propylene.

7. The method of claim 1 wherein the phosphorus treated zeolite comprises phosphorus in an amount of about 0.1% to about 10% by weight of the phosphorus treated zeolite.

8. The method of claim 1 wherein the contacting occurs at ambient pressure.

9. The method of claim 1 wherein the contacting occurs at a pressure of about 1 psig to about 30 psig.

10. The method of claim 1 wherein the contacting occurs at a temperature of about 600° F. to about 1,300° F.

11. The method of claim 1 further comprising steaming the catalyst prior to contacting the first mixture of C4+ compounds with the catalyst.

12. The method of claim 6, wherein at least one of the first mixture of C4+ compounds, the second mixture of C4+ compounds, and the third mixture of C4+ compounds is diluted with steam.

13. The method of claim 12, wherein at least one of the first mixture of C4+ compounds, the second mixture of C4+ compounds, and the third mixture of C4+ compounds is diluted with about 5% to about 35% by weight of steam, based on the weight of the first mixture of C4+ compounds, the second mixture of C4+ compounds, and the third mixture of C4+ compounds, respectively.

14. A method of producing at least one of ethylene and propylene, the method comprising:
   contacting a tailstream of a methanol-to-olefin process with a catalyst comprising:
   (a) a phosphorus treated zeolite, wherein the phosphorus treated zeolite comprises an alkali metal, and wherein the alkali metal is present in an amount no greater than about 0.5% by weight of the phosphorus treated zeolite, and
   (b) a binder, wherein the binder comprises bentonite, silica and kaolin, wherein the bentonite, silica and kaolin are present in the binder in a bentonite:silica:kaolin weight ratio of about 1:8-16:20-28,
   thereby producing an effluent comprising at least one of ethylene and propylene,
   wherein the tailstream comprises a plurality of C4+ compounds, and the catalyst converts at least a portion of the plurality of C4+ compounds to at least one of ethylene and propylene.

15. The method of claim 14, further comprising separating the ethylene and/or propylene from the effluent to form a first mixture of C4+ compounds, and contacting the first mixture of C4+ compounds with the catalyst to convert at least a portion of the first mixture of C4+ compounds to at least one of ethylene and propylene, thereby producing a first effluent comprising at least one of ethylene and propylene.

16. The method of claim 15, further comprising separating the ethylene and/or propylene from the first effluent to form a second mixture of C4+ compounds, and contacting the second mixture of C4+ compounds with the catalyst to convert at least a portion of the second mixture of C4+ compounds to at least one of ethylene and propylene.

17. The method of claim 14 wherein the catalyst is a fixed bed catalyst.

18. The method of claim 17 wherein the bentonite, silica and kaolin are present in a bentonite:silica:kaolin weight ratio of about 1:10-14:22-26.

19. A method of producing at least one of ethylene and propylene, the method comprising:
   providing a first mixture of C4+ compounds comprising a first plurality of C4+ olefins in an amount of at least 30% by weight of the first mixture of C4+ compounds; and
   contacting the first mixture of C4+ compounds with a catalyst comprising:
   (a) a phosphorus treated zeolite, wherein the phosphorus treated zeolite comprises an alkali metal, and wherein the alkali metal is present in an amount no greater than about 0.5% by weight of the phosphorus treated zeolite, and
   (b) a binder, wherein the binder comprises bentonite, silica and kaolin, wherein the bentonite, silica and kaolin are present in the binder at a bentonite:silica:kaolin weight ratio of about 1:8-16:20-28,
   to convert the first mixture to a reactor effluent comprising a second plurality of C4+ olefins and at least one of ethylene and propylene, wherein at least 15% by weight of the first plurality of C4+ olefins of the first mixture is converted to at least one of ethylene and propylene; and
   contacting the reactor effluent with the catalyst to convert at least a portion of the second plurality of C4+ olefins to at least one of ethylene and propylene.

20. The method of claim 19, wherein the catalyst is a fixed bed catalyst.

* * * * *

UNITED STATES PATENT AND TRADEMARK OFFICE
CERTIFICATE OF CORRECTION

| | |
|---|---|
| PATENT NO. | : 10,519,078 B2 |
| APPLICATION NO. | : 16/165630 |
| DATED | : December 31, 2019 |
| INVENTOR(S) | : Fang |

It is certified that error appears in the above-identified patent and that said Letters Patent is hereby corrected as shown below:

In the Specification

In Column 6, Line 30, delete "0.1" and insert -- 0.1% --, therefor

In Column 8, Line 46, delete "0.5," and insert -- 0.5%, --, therefor

In Column 8, Line 54, delete "10" and insert -- 10% --, therefor

Signed and Sealed this
Twelfth Day of July, 2022

Katherine Kelly Vidal
*Director of the United States Patent and Trademark Office*